United States Patent
Raney

(10) Patent No.: US 7,377,903 B2
(45) Date of Patent: May 27, 2008

(54) SPLIT TIP EXPRESSION DEVICE

(75) Inventor: Charles C. Raney, Camdenton, MO (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 210 days.

(21) Appl. No.: 10/794,957

(22) Filed: Mar. 5, 2004

(65) Prior Publication Data

US 2005/0197666 A1    Sep. 8, 2005

(51) Int. Cl.
*A61B 5/00* (2006.01)
*B65D 81/00* (2006.01)

(52) U.S. Cl. ..................... 600/583; 600/573
(58) Field of Classification Search ............ 600/573, 600/576, 583; 606/181, 182, 183
See application file for complete search history.

(56) References Cited

U.S. PATENT DOCUMENTS

| | | | |
|---|---|---|---|
| 4,360,016 A | 11/1982 | Sarrine | |
| 4,920,977 A * | 5/1990 | Haynes | 600/583 |
| 5,217,480 A | 6/1993 | Haber et al. | |
| 5,951,493 A | 9/1999 | Douglas et al. | |
| 6,176,865 B1 | 1/2001 | Mauze et al. | |
| 6,306,152 B1 * | 10/2001 | Verdonk et al. | 606/182 |
| 6,537,242 B1 * | 3/2003 | Palmer | 604/22 |
| 6,706,000 B2 * | 3/2004 | Perez et al. | 600/583 |
| 6,752,817 B2 * | 6/2004 | Flora et al. | 606/181 |
| 6,849,052 B2 * | 2/2005 | Uchigaki et al. | 600/584 |
| 2002/0138040 A1 | 9/2002 | Flora et al. | |
| 2002/0187556 A1 | 12/2002 | Shartle et al. | |
| 2003/0060730 A1 * | 3/2003 | Perez | 600/576 |
| 2004/0133127 A1 * | 7/2004 | Roe et al. | 600/583 |

FOREIGN PATENT DOCUMENTS

WO    WO 00/74763 A1    12/2000

* cited by examiner

*Primary Examiner*—Max F. Hindenburg
*Assistant Examiner*—Jonathan M Foreman
(74) *Attorney, Agent, or Firm*—Woodard, Emhardt, Moriarty, McNett & Henry LLP

(57) ABSTRACT

An expression device for a lancing device of the type that directs a skin-lancing medium against a skin site to make an incision for testing bodily fluids. The expression device has a pair of skin-engaging tabs curved and oriented to make the skin taut adjacent a lancet used with the device. This increases the incision width and enhances the quantity of blood removed for subsequent testing.

40 Claims, 2 Drawing Sheets

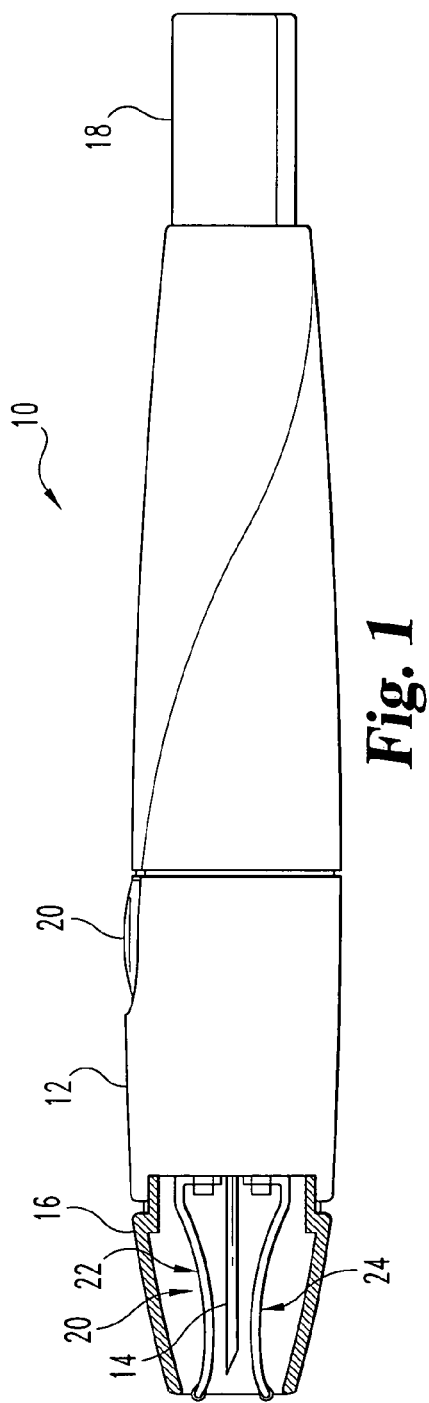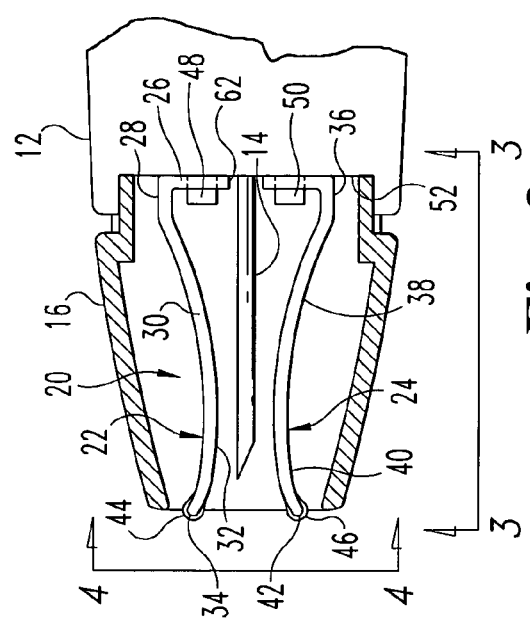
Fig. 1
Fig. 2

US 7,377,903 B2

SPLIT TIP EXPRESSION DEVICE

FIELD OF THE INVENTION

The present invention relates to devices for obtaining samples of blood and other fluids from the body for analysis or processing.

BACKGROUND OF THE INVENTION

Many medical procedures in use today require a relatively small sample quantity of bodily fluid such as blood for purposes of determining glucose levels. There are a number of home testing kits available for this purpose. Generally speaking, these kits include lancet mechanisms set up so that a lancing medium can make a controlled incision on the skin surface. The skin in the area of the incision is then expressed to obtain a sufficient size blood droplet for exposure to a test strip. In other forms, these devices have a lancing medium that may be needle-like or blade-like in configuration. The lancing medium may be used solely for the purposes of making an incision on the skin or it may additionally contain capillary and other passages to allow the blood to flow to a testing device.

In any event, once an incision has been made, the skin must be manipulated in such a way that an appropriate quantity of blood may be expressed. Typically this has been done by manual compression of the incision site which is a relatively coarse and crude method of massaging the skin for expression. Other approaches involve various forms of vibratory, ultrasonic, thermal stimulation, and mechanical kneading for blood expression. While more effective, these approaches add complexity and cost to the unit.

SUMMARY OF THE INVENTION

The present invention relates to an apparatus for sampling bodily fluid. The apparatus comprises a housing and a skin-lancing mechanism mounted in the housing for applying a skin-lancing medium against a skin surface to form an incision and then remove the skin-lancing medium from the incision. A device is mounted in the housing and has a plurality of skin-engaging elements oriented to urge the skin taut adjacent the incision site on said skin to at least open the incision.

In a further form of the invention, the skin-engaging elements act to express bodily fluid after the incision.

BRIEF DESCRIPTION OF THE DRAWINGS

FIG. 1 shows a lancet device usable to make an incision on the skin for bodily fluid sampling with an expression device embodying the present invention.

FIG. 2 is an enlarged fragmentary view of the bodily fluid expression device of FIG. 1.

DESCRIPTION OF THE SELECTED EMBODIMENTS

Figure 3:
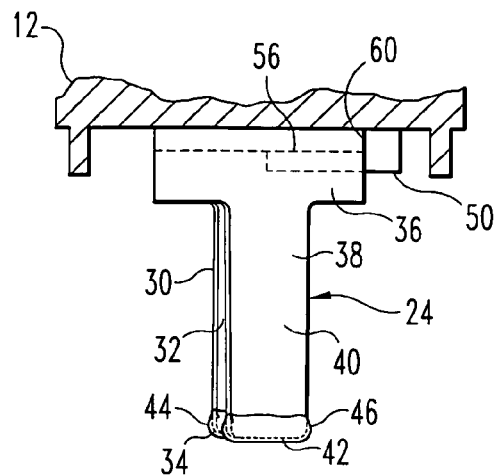
FIG. 3 shows a side view of the bodily fluid expression device of FIG. 2 taken in the direction of lines 3-3 of FIG. 2 with an external cap removed.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention uses a plurality of skin engaging elements in a lancing device to make the skin taut to at least open the incision made by the device.

FIG. 1 shows a lancet device 10 comprising a housing 12 having a mechanism to actuate a lancet 14 in a controlled fashion to make an incision on skin that is positioned against the open end of an exterior cap 16. The mechanism advances the lancet 14 at a controlled rate to a pre-selected depth to achieve an optimum cut.

The actuation mechanism will not be described in detail to simplify the understanding of the present invention. However, a plunger 18 is depressed into housing 12 to load a spring mechanism (not shown) that acts as the driver for the lancet 14. Various adjustable elements (not shown) on the device 10 are used to set the penetration depth of the lancet 14 when it is released. A release button 20 is depressed after the cap 16 is applied against the skin causing the lancet to pierce the skin and then retract to the position shown in FIG. 1. It is also possible to use the pressure of cap 16 against a skin site through an interconnection (not shown) with the lancet actuating mechanism to displace lancet 14. Lancet 14 is removable so that it may be disposed in appropriate fashion after a test is completed. Although making a mechanical incision is described for piercing the skin, it should be apparent that other mechanisms for making an incision, such as a laser, could be used with the present invention.

The actuation mechanism for lancet 14 may take one of many different forms to achieve a controlled rate of displacement and penetration depth. The actuator may be mechanical in form using a spring-like device. It may also be electrically or pneumatically actuated. As herein shown, lancet 14 may pierce the skin so that a sufficient quantity of blood may accumulate on the skin for application to a test strip (not shown). It should be noted that to those skilled in the art, the unit may be used to collect blood samples through the lancet 14 and provide still another way to integrate the testing process.

The advantages and features of the present invention will be seen to be equally applicable to the range of devices used to sample blood for glucose measurement and other applications. More specifically, the invention would be applicable to devices that sample and analyze the blood in a single unit.

In accordance with the present invention, the expression device 22 set forth in FIGS. 1-4 is employed to enhance the expression process. Expression device 20 is shown herein as a pair of flexible tabs 22 and 24 which extend from an integral base 26. Tab 22 has an initial section 28 extending at a right angle from base 26. An intermediate section 30 curving in towards lancet 14 and an end section 32 curving away from lancet 14 terminate in a tip 34. Tab 24 has an initial section 36 extending at a right angle from base 26, an intermediate section 38 curving in towards lancet 14, and an additional section 40 curving away from lancet 14 and terminating in an end 42. As shown in FIG. 2 especially, the length of tabs 22 and 24 is such that the edges 34 and 42 extend beyond lancet 14 in its retracted state either before or after the incision event. As shown particularly in FIGS. 3 and 4, edges 34 and 42 are elongated. As described later, edges 34 and 42 may have friction enhancing surfaces 44 and 46, respectively, herein shown as a rubber-like overlay.

Expression element 20 may be formed from an appropriate material giving sufficient flexibility to urge tips 34 and 42 away from lancet 14 when they are pressed against a skin surface. If the expression device 20 is formed from plastic or metal having a relatively low-friction surface characteristic, the addition of friction enhancing edges 44 and 46 may be employed. This may take the form of rubber or other material appropriate for molding on the edges 34 and 42.

The expression device 20 is removable so that lancet 14 may be replaced in a fashion in keeping with commercially available lancet devices. As shown herein, a pair of fingers 48 and 50 are secured to end 52 of housing 12. Fingers 48 and 50 may be attached in appropriate fashion as with adhesives or discrete fasteners. Fingers 48 and 50 each have slots 54 and 56, respectively, which receive base 26. Slots 54 and 56 have end walls 58 and 60 which form a limit and a means for positioning base 26 so that lancet 14 is central. Base 26 has a slot at 62 which permits base 26 to slide out of slots 54 and 56 so that lancet 14 may be removed. Although the expression device 20 is shown as removably positioned in housing 12 by means of fingers, it should be apparent to those skilled in the art that the expression device 20 could be mounted using equivalent elements like a hinged mounting.

Figure 4:
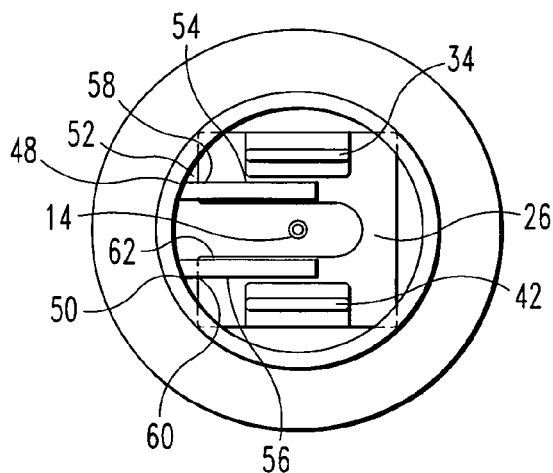
FIG. 4 shows an end view of the bodily fluid expression device of FIG. 2 taken in the direction of lines 4-4 of FIG. 2.
Figure 5:
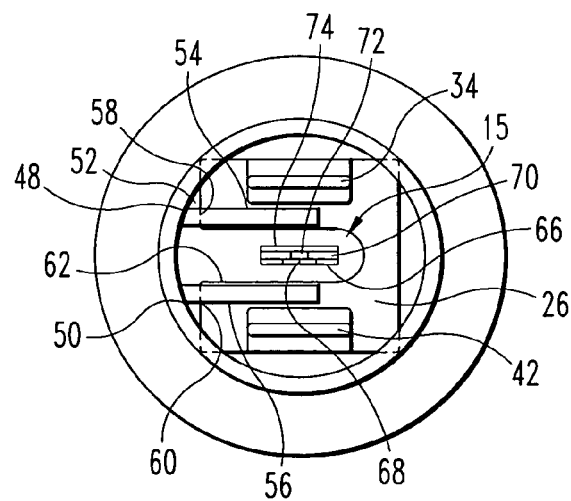
FIG. 5 shows an end view of the bodily fluid expression device of FIG. 2 but with an alternative lancet shape

When it is desired to operate the lancet device 10, the plunger 18 is cocked as is normal practice and the unit advanced so that edges 34 and 42 are placed against the skin. Because the sections of tabs 22 and 24 immediately preceding the edges are angled away from the lancet 14 and the tabs extend beyond lancet 14 in this condition, the edges 34 and 42 are urged apart to draw the skin taut. When the lancet is fired by depressing button 20, the incision is efficiently made and the edges 34 and 42 act to widen the incision which in turn causes an increase in blood flow. When the plunger is retracted, further urging of the expression device 20 will cause additional quantity of blood to generate sufficient quantities so that a test strip may be applied to the blood thus collected. In the alternative, if lancet 14 functions as a capillary, the quantity of blood would be transmitted by capillary action to an appropriate sampling device. Depending upon the relative dimensions of tabs 22, 24 and cap 16, cap may be left in place or removed for the lancing operation Although lancet 14 of FIG. 4 is shown having a circular cross-section, a blade type lancet 15 as shown in FIG. 5 may be employed so that the orientation of the blade and cut is generally parallel to the edges 34 and 42 as shown particularly in FIG. 5. The lancet 15 comprises a blade-like cutting element 66 having a pointed skin-piercing section 68. It should be noted, however, that the piercing section may have a different configuration. The cutting element 66 is attached to a spacer element 70 to define a capillary passage 72, defined on the opposite side by a base element 74. The capillary passage 72 carries bodily fluid from the incision made by piercing section 68 to a test strip (not shown) that indicates a parameter of the bodily fluid. As a result, the expansion of the wound made by the blade-like cutting element 66 is maximized and made most efficient which is particularly beneficial when the device incorporates an integrated lancing test strip using a blade-like incision.

It can then be seen that the device thus proposed is a highly simple but effective way for maximizing the bodily fluid produced in a lancing operation.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. Apparatus for sampling bodily fluid, said apparatus comprising:
    a housing,
    a skin-lancing device mounted in said housing for directing a skin-lancing medium against a skin surface to form an incision therein, and then remove the skin-lancing medium from the incision,
    a device mounted in said housing, said device having a pair of elongated skin-engaging flexible tabs, each tab having a length and defining a centerline extending through the center of said tab along said length, said tabs oriented to urge the skin taut adjacent the incision site on said skin to at least open the incision, said tabs extending from a base to adjacent the incision, each said tab having an intermediate section wherein said centerline extends toward the skin surface and toward said skin-lancing medium, and each said tab having a section adjacent the skin surface wherein said centerline extends toward the skin surface and away from said skin-lancing medium.

2. Apparatus as claimed in claim 1 wherein the pair of skin-engaging flexible tabs act to express bodily fluid after incision.

3. Apparatus as claimed in claim 1 wherein the pair of skin-engaging flexible tabs hold the skin taut before incision.

4. Apparatus as claimed in claim 1 wherein said tabs have friction enhancing surfaces on their tips for engaging the skin.

5. Apparatus as claimed in claim 1 wherein said tabs extend beyond the lancing medium in its condition prior to lancing said skin.

6. Apparatus as claimed in claim 1 further comprising a removable cap over said skin lancing device and said skin engaging flexible tabs.

7. Apparatus as claimed in claim 1 further comprising a cap attached to said housing for contacting the skin on opposing sides of the incision.

8. Apparatus as claimed in claim 1 wherein each said skin-engaging flexible tab has an elongated tip, said pair of elongated tips having parallel line contacts with the skin.

9. Apparatus as claimed in claim 1 wherein said centerline in said intermediate section extends toward said skin-lancing medium when said tab is pressed against the skin, and wherein said centerline in said section adjacent the skin surface extends away from said skin-lancing medium when said tab is pressed against the skin.

10. Apparatus as claimed in claim 1 wherein said centerline in said intermediate section curves toward said skin-lancing medium and said centerline in said section.

11. Apparatus as claimed in claim 1 wherein said base is removable from said housing.

12. Apparatus as claimed in claim 11 further comprising clips mounted on said housing and having slots into which said base extends, said base having a slot surrounding the site for said lancing medium to permit sideways removal from said base.

13. Apparatus as claimed in claim 1 wherein said pair of skin-engaging flexible tabs are opposed from one another and have line contact with the skin, said lancing medium being a blade-like lancet extending parallel to said opposed line contacts.

14. Apparatus as claimed in claim 13 wherein said lancing medium further comprises a capillary passage adjacent said blade-like lancet to carry bodily fluid from said incision.

15. Apparatus as claimed in claim 14 wherein said capillary passage is parallel to said lancing medium.

16. Apparatus as claimed in claim 14 wherein said capillary passage is bounded on one side by said lancing medium.

17. A method of sampling bodily fluid from an incision m a skin site comprising:
providing a skin lancing device having a pair of flexible tabs extending alongside said skin lancing device to elongated skin-engaging edges, said tabs having an intermediate section extending toward the skin surface and toward said skin lancing device, and a section adjacent the elongated skin-engaging edges extending toward the skin surface and away from said skin lancing devices;
making an incision;
engaging the skin along straight lines with said elongated skin-engaging edges;
pressing said elongated skin-engaging edges against said skin to stretch the skin taut at said site to at least open the incision; and
urging said elongated skin-engaging edges away from said skin lancing device.

18. A method as claimed in claim 17 further comprising carrying bodily fluid from the incision by a capillary passage adjacent the skin lancing device.

19. A method as claimed in claim 17 wherein the pair of flexible tabs are elongated.

20. A method as claimed in claim 17 wherein said engaging the skin is along parallel straight lines.

21. A method as claimed in claim 17 wherein said elongated skin-engaging edges move in opposite directions away from one another.

22. A method as claimed in claim 17 further comprising the further step of stretching the skin taut prior to making an incision.

23. A method as claimed in claim 22 comprising the further step of expressing bodily fluid from the incision.

24. Apparatus for sampling bodily fluid, said apparatus comprising:
a housing,
a skin-lancing device mounted to said housing for directing a skin-lancing medium against a skin surface to form an incision therein, and for removing the skin-lancing medium from the incision,
a cap attached to said housing, said cap defining an interior and including a skin-engaging portion for contacting the skin, and
at least two flexible tabs, each tab attached to said housing and extending at least partially within said interior to a free end, each said free end including a skin-engaging edge, wherein said at least two skin-engaging edges are parallel, and said at least two flexible tabs are oriented to urge said skin-engaging edges in opposite directions away from one another when pressed against the skin.

25. Apparatus as claimed in claim 24 wherein each said flexible tab is elongated and includes an intermediate portion and an end portion, said end portion being adjacent said free end, wherein said at least two intermediate portions extend toward one another and said at least two end portions extend away from one another.

26. Apparatus as claimed in claim 24 wherein each said skin-engaging edge is elongated and engages the skin along a straight line, and wherein said at least two flexible tabs are oriented to urge said skin-engaging edges away from said skin-lancing medium to at least open the incision.

27. Apparatus as claimed in claim 24 wherein said cap contacts the skin surface after said skin-engaging edges when said cap is pressed against the skin surface.

28. Apparatus as claimed in claim 24 wherein said cap limits the urging of said two skin-engaging edges.

29. Apparatus as claimed in claim 24 wherein said cap is removable from said housing.

30. Apparatus as claimed in claim 24 wherein said skin-lancing medium comprises a blade-like lancet, said apparatus further comprising a capillary passage adjacent said blade-like lancet to carry bodily fluid from said incision.

31. Apparatus as claimed in claim 30 wherein said capillary passage is defined at least in part by said blade-like lancet.

32. Apparatus for sampling bodily fluid, said apparatus comprising:
a housing,
a skin-lancing device mounted in said housing for directing a skin-lancing medium against a skin surface defining a plane to form an incision therein, and for removing the skin-lancing medium from the incision,
at least two flexible tabs attached to said housing with said skin-lancing device positioned between said at least two flexible tabs, each tab extending from a base portion to a free end and including an intermediate portion between said base portion and said free end, each said free end including a skin-engaging edge, wherein said at least two flexible tabs are oriented to urge said skin-engaging edges in opposite directions away from one another when pressed against the skin,
wherein said at least two base portions, intermediate portions and free ends each include an inner surface facing said skin-lancing device, an outer surface facing away from said skin-lancing device, and a thickness separating said inner surface and said outer surface, wherein said base portion thickness, said intermediate portion thickness and said free end thickness are approximately equal,
wherein a distance separating said at least two intermediate portion inner surfaces and parallel to said skin surface plane is less than a distance separating said at least two base portion inner surfaces and parallel to said skin surface plane, and
wherein a distance separating said at least two intermediate portion inner surfaces and parallel to said skin surface plane is less than a distance separating said at least two free end inner surfaces and parallel to said skin surface plane.

33. Apparatus as claimed in claim 32 wherein each said skin-engaging edge has a straight line contact with the skin surface and said at least two skin-engaging edges are parallel.

34. Apparatus as claimed in claim 32 wherein said at least two flexible tabs are elongated and opposed from one another with each having line contact with the skin, said skin-lancing medium being a blade-like lancet with the orientation of the blade being parallel to said line contacts.

35. Apparatus for sampling bodily fluid, said apparatus comprising:
a housing,
a skin-lancing device with a central axis mounted to said housing for directing a skin-lancing medium against a skin surface to form an incision therein,
at least two flexible tabs mounted to said housing and extending from an upper base portion to a lower portion with a middle portion between said upper and lower portions, said lower portion including a skin-engaging end, said skin-engaging ends adapted to engage and stretch the skin surface between said skin-engaging ends, wherein each said at least two flexible tabs has an inner surface facing said skin-lancing device, an outer surface facing away from said skin-lancing device, and a thickness separating said inner surface and said outer surface, wherein said thickness is constant from said base to said skin-engaging end, and wherein each said inner surface is convex with said middle portion being nearer said skin-lancing device central axis than either said upper portion or said lower portion.

36. Apparatus as claimed in claim 35 wherein said at least two flexible tabs are adapted to urge said skin-engaging edges away from one another when pressed against the skin.

37. Apparatus as claimed in claim 35 wherein said at least two flexible tabs are elongated and opposed from one another with each having line contact with the skin, and wherein said skin-lancing device is a blade-like lancet with the orientation of the blade being parallel to said line contacts.

38. Apparatus for sampling bodily fluid, said apparatus comprising:

a housing, a skin-lancing device mounted in said housing for directing a skin-lancing medium against a skin surface to form an incision therein, and for removing the skin-lancing medium from the incision, at least two flexible tabs, each tab attached to said housing and extending to a free end, each said free end including a skin-engaging edge, wherein said at least two skin-engaging edges are parallel, and said at least two flexible tabs are oriented to urge said skin-engaging edges in opposite directions away from one another when pressed against the skin, and at least two flexible replacement tabs, wherein said flexible replacement tabs are interchangeably attachable to said housing with said at least two flexible tabs.

39. Apparatus for sampling bodily fluid, said apparatus comprising:

a housing, a skin-lancing device mounted in said housing for directing a skin-lancing medium against a skin surface to form an incision therein, and then remove the skin-lancing medium from the incision, a device mounted in said housing, said device having a pair of elongated skin-engaging flexible tabs, each tab having a length and defining a centerline extending through the center of said tab along said length, said tabs oriented to urge the skin taut adjacent the incision site on said skin to at least open the incision, said tabs extending from a base to adjacent the incision, each said tab having an intermediate section wherein said centerline extends toward said skin-lancing medium and a section adjacent the skin surface wherein said centerline extends away from said skin-lancing medium, wherein said base is removable from said housing, and clips mounted on said housing and having slots into which said base extends, said base having a slot surrounding the site for said lancing medium to permit sideways removal from said base.

40. Apparatus for sampling bodily fluid, said apparatus comprising:

a housing, a skin-lancing device mounted in said housing for directing a skin-lancing medium against a skin surface to form an incision therein, and then remove the skin-lancing medium from the incision, a device mounted in said housing, said device having a pair of elongated skin-engaging flexible tabs, each tab having a length and defining a centerline extending through the center of said tab along said length, said tabs oriented to urge the skin taut adjacent the incision site on said skin to at least open the incision, said tabs extending from a base to adjacent the incision, each said tab having an intermediate section wherein said centerline extends toward said skin-lancing medium and a section adjacent the skin surface wherein said centerline extends away from said skin-lancing medium, and a cap attached to said housing for contacting the skin on opposing sides of the incision.

* * * * *

UNITED STATES PATENT AND TRADEMARK OFFICE
CERTIFICATE OF CORRECTION

| | | |
|---|---|---|
| PATENT NO. | : 7,377,903 B2 | Page 1 of 1 |
| APPLICATION NO. | : 10/794957 | |
| DATED | : May 27, 2008 | |
| INVENTOR(S) | : Charles C. Raney | |

It is certified that error appears in the above-identified patent and that said Letters Patent is hereby corrected as shown below:

In column 4, line 52, change
"lancing medium and said centerline is said section." to -- lancing medium and said centerline in said section adjacent the skin surface curves away from said skin-lancing medium. --

In column 5, line 6, change
"A method of sampling bodily fluid from an incision m" to -- A method of sampling bodily fluid from an incision in --

In column 5, line 9, change
"alongside said skin lancing device to" to -- alongside the skin lancing device to --

In column 5, line 10, change
"elongated skin-engaging edges, said tabs having an" to -- elongated skin-engaging edges, the tabs having an --

In column 5, line 15, change
"lancing devices" to -- lancing device --

Signed and Sealed this

Twelfth Day of August, 2008

JON W. DUDAS
*Director of the United States Patent and Trademark Office*